United States Patent
Tsoupas

(10) Patent No.: US 9,550,077 B2
(45) Date of Patent: Jan. 24, 2017

(54) MULTI TURN BEAM EXTRACTION FROM SYNCHROTRON

(71) Applicant: Brookhaven Science Associates, LLC, Upton, NY (US)

(72) Inventor: Nicholaos Tsoupas, East Moriches, NY (US)

(73) Assignee: Brookhaven Science Associates, LLC, Upton, NY (US)

( * ) Notice: Subject to any disclaimer, the term of this patent is extended or adjusted under 35 U.S.C. 154(b) by 197 days.

(21) Appl. No.: 14/317,237

(22) Filed: Jun. 27, 2014

(65) Prior Publication Data

US 2015/0005567 A1     Jan. 1, 2015

Related U.S. Application Data

(60) Provisional application No. 61/840,147, filed on Jun. 27, 2013.

(51) Int. Cl.
*H05H 7/10*    (2006.01)
*A61N 5/10*    (2006.01)

(52) U.S. Cl.
CPC ............. *A61N 5/1077* (2013.01); *H05H 7/10* (2013.01); *A61N 2005/1087* (2013.01)

(58) Field of Classification Search
None
See application file for complete search history.

(56) References Cited

U.S. PATENT DOCUMENTS

| | | | | |
|---|---|---|---|---|
| 5,073,913 A | * | 12/1991 | Martin | H05H 9/00 315/503 |
| 5,898,261 A | * | 4/1999 | Barker | H05H 7/00 313/20 |
| 6,173,036 B1 | * | 1/2001 | Hossain | G01N 23/223 378/45 |
| 6,201,851 B1 | * | 3/2001 | Piestrup | H05G 2/00 378/121 |
| 6,605,473 B1 | * | 8/2003 | Hajduk | B01J 19/0046 378/208 |
| 7,432,516 B2 | | 10/2008 | Peggs et al. | |

(Continued)

OTHER PUBLICATIONS

Tsoupas, N. et al., "Design Of Beam-Extraction Septum Magnet For The SNS", Proceedings of the, Proceedings of the 2001 Particle Accelerator Conference, Chicago, 2001, pp. 3245-3247.

(Continued)

*Primary Examiner* — Douglas W Owens
*Assistant Examiner* — Srinivas Sathiraju
(74) *Attorney, Agent, or Firm* — Dorene M. Price; Lars O. Husebo

(57) ABSTRACT

This disclosure relates to apparatuses and methods for the extraction of particle beams while maintaining the energy levels and precision of the particles and the particle beam. Apparatuses and methods for extracting a charged particle beam from a central orbit in a synchrotron are provided, in which a particle beam is deflected from the central orbit. Parts of the deflected particle beam passes through a stripping foil placed in at least parts of the deflected path such that the particles that pass through the foil are stripped of at least one electron. The electron stripped particles and the non-stripped particles may be separated magnetically.

29 Claims, 3 Drawing Sheets

(56) References Cited

U.S. PATENT DOCUMENTS

| | | | |
|---|---|---|---|
| 8,109,865 B2 * | 2/2012 | Jackson | A61N 5/10 600/1 |
| 8,399,866 B2 | 3/2013 | Balakin | |
| 8,415,643 B2 | 4/2013 | Balakin | |
| 8,581,523 B2 * | 11/2013 | Gall | H05H 13/02 315/501 |
| 8,718,231 B2 * | 5/2014 | Balakin | A61B 6/032 250/492.3 |
| 8,952,634 B2 * | 2/2015 | Sliski | H05H 13/02 315/502 |
| 8,970,137 B2 * | 3/2015 | Gall | H05H 13/02 315/501 |
| 9,056,199 B2 * | 6/2015 | Balakin | A61N 5/10 |
| 9,095,705 B2 * | 8/2015 | Trbojevic | A61N 5/1043 |
| 9,155,911 B1 * | 10/2015 | Balakin | A61N 5/1081 |
| 9,168,392 B1 * | 10/2015 | Balakin | A61N 5/1049 |
| 9,302,122 B2 * | 4/2016 | Balakin | A61N 5/1081 |
| 9,314,649 B2 * | 4/2016 | Balakin | A61N 5/107 |
| 2010/0230620 A1 * | 9/2010 | Tsoupas | A61N 5/10 250/522.1 |
| 2013/0217946 A1 * | 8/2013 | Balakin | A61N 5/10 600/1 |
| 2014/0163301 A1 * | 6/2014 | Trbojevic | A61N 5/1043 600/1 |

OTHER PUBLICATIONS

Trbojevic, D. et al., "Lattice Design Of A Rapid Cycling Medical Synchrotron For Carbon/Proton Therapy", Proceedings of IPAC2, Proceedings of IPAC2011, San Sebastian, Spain, 2011, pp. 2541-2543.

Tsujii, H. and Kamada, T., "A Review of Update Clinical Results of Carbon Ion Radiotherapy", Jpn J Clin Oncol 2012, 42, Jpn J Clin Oncol 2012, 42 (8), pp. 670-685.

* cited by examiner

MULTI TURN BEAM EXTRACTION FROM SYNCHROTRON

CROSS-REFERENCE TO A RELATED APPLICATION

This application claims the benefit under 35 U.S.C. 119(e) of U.S. Provisional Application No. 61/840,147 filed on Jun. 27, 2013, the content of which is incorporated herein in its entirety.

STATEMENT OF GOVERNMENT LICENSE RIGHTS

This invention was made with government support under contract number DE-AC02-98CH10886, awarded by the U.S. Department of Energy. The United States government has certain rights in the invention.

FIELD OF THE INVENTION

This disclosure relates to particle extraction within an accelerator used in various applications for treatment of a patient.

BACKGROUND

Particle accelerators are apparatuses that are used for accelerating subatomic particles to high velocities by means of electric or electromagnetic fields. When particles are accelerated to reach a specific energy, they are used for treatment of patients with malignant tumors. The particles may be accelerated either in a straight line, in which the particles are accelerated within a specific distance, or the particles may be accelerated in a circular accelerator. The circular accelerator moves clusters of particles in a circle (or oval), and with each completion of the circle, the cluster of particles gains energy until the particles have reached sufficient energy levels, at which point the particles may be extracted and directed to the tumor.

Extraction is the process of removing a particle beam from the accelerator to a transfer line or a beam dump, at the appropriate time, while minimizing the beam loss, and placing the extracted particles into a desired trajectory. One method of extracting a proton particle beam is described in U.S. Pat. No. 7,432,516, the content of which is incorporated herein by reference in its entirety. The method includes initiating a kicker magnet which turns on a vertical magnetic field that moves the particle beam horizontally towards a septum magnet which further bends the beam horizontally and away from the accelerator and into a beam line which guides the beam to the tumor of the patient. However, due to limitations on the level of radiation acceptable to a patient, and challenges in accelerating and controlling low numbers of carbon particles in the accelerator, such extraction methods may be less suitable for carbon particles. Another method of extracting a particle beam is described in U.S. Pat. Nos. 8,415,643 and 8,399,866. The method includes passing the beam through a radio-frequency cavity system to induce oscillation of a charged particle stream. With sufficient amplitude modulation the particles hit an energy reducing foil which decreases the energy of the charged particle stream and decreases the radius of curvature sufficiently to allow physical separation of the reduced-energy particle stream from the original particle stream. However, with this method, not only may the extracted particle beam have less energy than the original beam, the extracted particle beam may also have a higher energy spread resulting in less precision of the particle beam. Furthermore, this method may also result in beam particle loss as well as residual activity in the relatively thick energy reducing foil.

Therefore, there is a need for an apparatus and method which may be used on the extraction of carbon particle beams while maintaining the energy levels and precision of the particles and the particle beam.

SUMMARY OF THE INVENTION

Embodiments of the invention relate to apparatuses and methods for the extraction of particle beams while maintaining the energy levels and precision of the particles and the particle beam.

An embodiment provides an apparatus for extracting a charged particle beam from a central orbit in a synchrotron. The apparatus includes: at least one first magnet positioned to deflect the charged particle beam from the central orbit to a deflected path; at least one stripping foil placed in at least parts of the deflected path, wherein at least a portion of the charged particle beam passing through the stripping foil becomes a stripped charged particle beam; at least one second magnet encompassing the central orbit, the stripped charged particle beam, and a remaining charged particle beam, whereby paths of the stripped charged particle beam and the remaining charged particle beam are separated, the path of the stripped charged particle beam being separated further away from the central orbit than is the path of the remaining charged particle beam; and at least one particle retainer positioned to return the remaining charged particle beam to the central orbit.

In another embodiment, an apparatus for delivering a charged particle beam to treat malignant tissue is provided. The apparatus includes: a synchrotron having a central orbit; at least one first magnet positioned to deflect the charged particle beam from the central orbit to a deflected path; at least one stripping foil placed in at least parts of the deflected path, wherein the charged particle beam passing through the stripping foil becomes a stripped charged particle beam; a second magnet encompassing the central orbit, the stripped charged particle beam, and a remaining charged particle beam, whereby paths of the stripped charged particle beam and the remaining charged particle beam are separated, the path of the stripped charged particle beam being separated further away from the central orbit than is the path of the remaining charged particle beam; at least one particle retainer positioned to return the remaining charged particle beam to the central orbit; and a treatment path for delivering the stripped charged particle beam to the malignant tissue.

In another embodiment, an apparatus for extracting a charged particle beam from a central orbit in a synchrotron is provided. The apparatus includes: at least one extractor positioned to deflect the charged particle beam from the central orbit to a deflected path; at least one stripping foil placed in at least parts of the deflected path, wherein the charged particle beam passing through the stripping foil becomes a stripped charged particle beam; a multi-pole magnet encompassing the central orbit, the stripped charged particle beam, and a remaining charged particle beam, whereby paths of the stripped charged particle beam and the remaining charged particle beam are separated, and the path of the stripped charged particle and the path of the remaining charged particle beam are separated from the central orbit; and at least one particle retainer positioned to return the remaining charged particle beam to the central orbit.

Any of the apparatuses described above may have any combination of the following attributes:

- a septum to further separate the path of the stripped charged particle beam away from the central orbit.
- the at least one first magnet positioned to deflect the charged particle beam comprises at least one dipole magnet.
- the at least one second magnet comprises at least one dipole magnet.
- the at least one second magnet further comprises a multipole magnet.
- the at least one particle retainer comprises at least two dipole magnets.

In a further embodiment, a method for extracting a charged particle beam from a central orbit in a synchrotron is provided. The method includes: introducing the charged particle beam from an ion source and into the central orbit; activating at least one extractor positioned to deflect the charged particle beam from the central orbit; passing at least parts of the charged particle beam through at least one stripping foil to provide a stripped charged particle beam; passing the stripped charged particle beam and a remaining charged particle beam through at least one magnet encompassing the central orbit, the stripped charged particle beam, and the remaining charged particle beam, such that the paths of the stripped charged particle beam and the remaining deflected charged particle beam are separated, and the path of the stripped charged particle beam is separated further away from the central orbit than is the path of the remaining charged particle beam; and activating at least one particle retainer such that the remaining charged particle beam is returned to the central orbit.

In yet another embodiment, a method for delivering a charged particle beam to treat malignant tissue is provided. The method includes: introducing the charged particle beam from an ion source and into a central orbit of a synchrotron; activating at least one extractor positioned to deflect the charged particle beam from the central orbit to form a deflected charged particle beam; allowing at least parts of the deflected charged particle beam to pass through at least one stripping foil such that the deflected charged particle beam passing through the stripping foil becomes a stripped charged particle beam; passing the stripped charged particle beam and a remaining deflected charged particle beam through a multi-pole magnet encompassing the central orbit, the stripped charged particle beam, and the remaining deflected charged particle beam, such that the paths of the stripped charged particle beam and the remaining deflected charged particle beam are separated, and the path of the stripped charged particle beam is separated further away from the central orbit than is the path of the remaining deflected charged particle beam; activating at least one particle retainer such that the remaining deflected charged particle beam is returned to the central orbit; and delivering the stripped charged particle beam to treat malignant tissue.

Any of the methods described above may have any combination of the following attributes:

- the method may further involve activating a septum to further separate the path of the stripped charged particle beam away from the central orbit.
- the at least one extractor comprises at least one dipole magnet.
- the at least one particle retainer comprises at least two dipole magnets.
- the at least one magnet encompassing the central orbit, the stripped charged particle beam, and the remaining charged particle beam comprises at least one dipole magnet.
- the at least one magnet encompassing the central orbit, the stripped charged particle beam, and the remaining charged particle beam further comprises at least one multipole magnet.
- the charged particle beam first comprises between about $10^6$ and about $10^{10}$ ion particles per particle bunch, or between about $10^7$ and about $10^9$ ion particles per particle bunch.
- the stripped charged particle beam comprises between about $1.0 \times 10^4$ and about $8.5 \times 10^4$ ion particles per stripped particle bunch.
- the charged particle beam comprises $C^{+5}$ particles.
- the stripped charged particle beam comprises $C^{+6}$ particles.
- introducing the charged particle beam from an ion source and into the central orbit is performed at a frequency between about 1 Hz and about 75 Hz such as between between about 10 Hz and 20 Hz, or between about 10 Hz and 15 Hz.

DESCRIPTION OF THE DRAWINGS

These and other features, aspects, and advantages of the present invention will become better understood with regard to the following description, appended claims, and accompanying drawings where:

DETAILED DESCRIPTION

Figure 1:
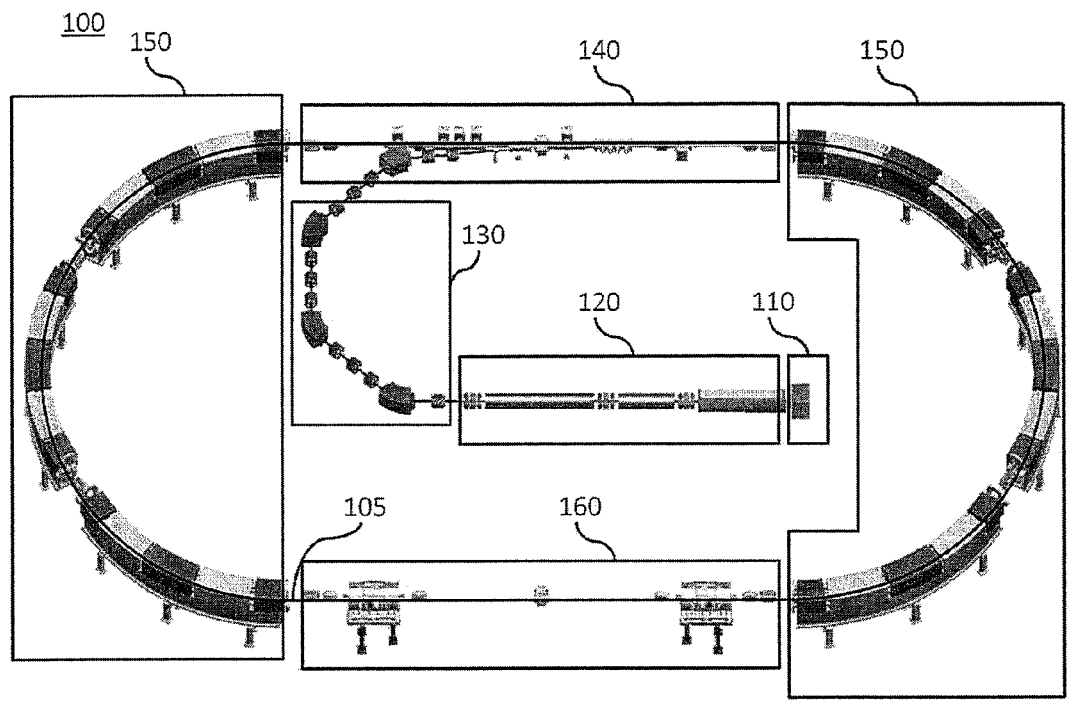
FIG. 1 is a diagram illustrating a system configuration of a circular accelerator, according to an embodiment of the invention.

In the Summary of the Invention above and in the Detailed, and the claims below, and in the accompanying drawings, reference is made to particular features (including method steps) of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with and/or in the context of other particular aspects and embodiments of the invention, and in the invention generally.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a, first number)(a second number)," this means a range whose lower limit is the first number and whose upper limit is the second number. For example, 25 to 100 mm means a range whose lower limit is 25 mm, and whose upper limit is 100 mm.

The maximum kinetic energy of ions required to treat cancerous tumors in the human body is 206 Mev for protons and 400 MeV/u for carbon. At these energies the range of the protons and carbon ions in the human body is 27 cm; a range that is adequate to irradiate any size of tumor at any location of the body. A constraint is that a maximum dose of 2.5 Gy per treatment is allowed to be delivered to any part of the human body including the tumor. Of further consideration is the multiple scattering and the energy straggling that ions experience when traveling in the human body. The semi-empirical formulas (1) and (2) below (taken from Nobuyuki Kanematsu 2009 *Phys. Med. Biol.* 54 N67) can be used to calculate these quantities.

$$\sigma_{x,y} = 0.0294 R^{0.896} Z^{-0.207} A^{-0.396}$$
(1) Multiple scattering of a pencil beam $$\sigma_z = 0.012 R^{0.951} A^{-0.5}$$
(2) Energy straggling of a pencil beam In formulas (1) and (2) above, the symbols A, Z and R are the mass number, the atomic number, and the range in cm of the irradiating ion, respectively. Using the above formulas it can be calculated that a 206 MeV pencil-like proton beam is spread out in a voxel volume of 714.7 mm$^3$, and the required value of protons per bunch to deliver the maximum allowed dose of ~2.5 Gy in the voxel is ~5.4×10$^7$. For a 400 MeV/u carbon pencil like beam which has the same range of 27 cm as the 206 MeV proton beam the formulas (1) and (2) above yield a voxel volume of 13.8 mm$^3$, therefore the required number of carbon ions per beam bunch to deliver the dose of 2.5 Gy in a voxel is 4.5×10$^4$. Table 1 summarizes the results of the comparison of 206 MeV protons with the 400 MeV/u carbon ions. The reduced effect of the multiple scattering and energy straggling on the carbon ions shown in columns 4 and 5, respectively, generates a reduced voxel volume of 13.8 mm$^3$ as compared to that of the protons of 714.7 mm$^3$ (column 6). The reduced voxel volume for carbon ions in combination with the upper limit on the allowed dose of 2.5 Gy, contribute to a long treatment time of about 80 minutes and a very small number of 4.5×10$^4$ carbon ions per bunch which may be too low for the control of the acceleration process.

TABLE 1

Comparison of protons and Carbon ions regarding tumor irradiation

| Ion | KE/u MeV/u | R cm | $2\sigma_{x,y}$ mm | $2\sigma_z$ mm | Voxel mm$^3$ | # of Voxels/lit | Time min | p/bunch |
|---|---|---|---|---|---|---|---|---|
| p | 206 | 27 | 11.35 | 5.55 | 714.7 | 1.4 × 10$^3$ | 1.5 | 5.4 × 10$^7$ |
| $^{12}$C | 400 | 27 | 2.93 | 1.61 | 13.8 | 7.25 × 10$^4$ | 80.0 | 4.5 × 10$^4$ |

Herein are described apparatuses and methods to overcome the long treatment time and the low number of ions per bunch, associated with carbon treatment. The apparatuses and methods allow the carbon bunch to contain the proper number of ions for optimum control of the acceleration, and also reduce the treatment time to irradiate a tumor of volume 1L, to less than 2 min, assuming a synchrotron repetition rate of 15 Hz.

Although the apparatuses and methods described herein may specially be useful for charged carbon particles, any suitable charged particles may be contemplated as long as the charged particles initially contain at least one electron readily available to be stripped from the charged particle. For example, suitable charged particles may include $H^{-1}$, $C^{+1}$, $C^{+2}$, $C^{+3}$, $C^{+4}$, and $C^{+5}$. In one embodiment, the charged particles are $C^{+5}$ particles.

FIG. 1 illustrates a system configuration of a synchrotron accelerator 100, according to an embodiment of the invention. Any suitable design of synchrotron accelerator 100 is contemplated. For example, the synchrotron may have the shape and components as described in U.S. Pat. No. 7,432,516. Embodiments of the invention encompass the synchrotron accelerator 100 having the shape of a race track, with two straight sections 140 and 160, and two 180 degree arc sections 150. The length of the two straight sections 140 and 160 may be between about 8 meters and about 20 meters long, such as from 9 to 15 meters long, or from 10 to 12 meters long. In one embodiment, the two straight sections 140 and 160 are about 10 meters long. In another embodiment, the two straight sections 140 and 160 are about 12 meters long. The two 180 degree arc sections 150 may have radiuses of between about 2 meters and 15 meters, such as between about 4 and 8 meters, between about 5 and 7 meters, or between about 6 and 6.5 meters. In an embodiment, the two 180 degree arc sections 150 have radiuses of about 5 meters. In another embodiment, the two 180 degree arc sections 150 have radiuses of about 6 meters. Within the synchrotron accelerator 100 is a central orbit 105. The central orbit 105 may be contained within a beam pipe having a diameter of at least 1 cm, for example between about 1 cm and about 10 cm. All individual values and subranges between about 1 cm and about 10 cm group are included herein and disclosed herein; for example, the diameter may be from a lower limit of about 1, 1.5, 2, 2.5, 3, 3.5, 4, 5, or 6 cm to an upper limit of about 2, 2.5, 3, 3.5, 4, 5, 6, 7, 8, 9, or 10, cm. In one embodiment, the beam pipe has a diameter of about 3 cm.

In the inner area of the synchrotron accelerator 100 is an ion source 110. Although depicted to be in the inner area of the synchrotron accelerator 100, depending on the synchrotron layout, the ion source 110 may alternatively be outside the area of the central orbit 105. The ion source 110 is connected to a pre accelerator 120, followed by an injection line 130.

The ion source 110, the pre accelerator 120, and the injection line 130, may be designed to inject between about 1 MeV/u and about 20 MeV/u protons or carbon ions. All individual values and subranges between about 1 MeV/u and about 20 MeV/u are included herein and disclosed herein; for example, the energy of the charged ions may be from a lower limit of about 1, 2, 3, 4, 5, 6, 7, 8, 9, 10, 11, 12, 14, 15, or 16 MeV/u to an upper limit of about 4, 5, 6, 7, 8, 9, 10, 11, 12, 14, 15, 16, 17, 18, 19, or 20 MeV. In one embodiment, the ion source 110, the pre accelerator 120, and the injection line 130, are designed to inject 8 MeV/u $C^{5+}$ ions.

The ion source 110 may be designed to provide charged particle bunches having up to about $10^{10}$ ion particles per bunch, such as for example between about $10^6$ and about $10^{10}$ ion particles per bunch. All individual values and subranges up to about $10^{10}$ ion particles per bunch are included herein and disclosed herein; for example, the number of ion particles per bunch may be from a lower limit of about $10^6$, $10^7$, $10^8$, or $10^9$, to an upper limit of about $10^7$, $10^8$, $2\times10^8$, $3\times10^8$, $4\times10^8$, $5\times10^8$, $6\times10^8$, $7\times10^8$, $8\times10^8$, $9\times10^8$, $10^9$, $2\times10^9$, $3\times10^9$, $4\times10^9$, $5\times10^9$, $6\times10^9$, $7\times10^9$, $8\times10^9$, $9\times10^9$ or $10^{10}$. In one embodiment, the ion source 110 may be designed to provide charged particle bunches having about $10^8$ ion particles per bunch.

The ion source 110 may be designed to provide charged particle bunches at a repetition rate of between about 1 Hz and 75 Hz. All individual values and subranges between about 1 Hz and about 75 Hz are included herein and disclosed herein; for example, the repetition rate may be from a lower limit of about 1, 2, 3, 4, 5, 6, 7, 8, 9, 10, 11, 12, 14, 15, 16, 17, 18, 19, 20, 25, 30, 35, or 40 Hz to an upper limit of about 5, 6, 7, 8, 9, 10, 11, 12, 14, 15, 16, 17, 18, 19, 20, 25, 30, 35, 40, 45, 50, 55, 60, 65, 70, or 75 Hz. In one embodiment the repetition rate is 15 Hz.

The particle bunches may injected into the central orbit 105 at one of the straight sections 140 and 160. In an embodiment, straight section 140 may serve as an injection/extraction section. The two 180 degree arc sections 150 may include several half cells with combined function magnets (FODO lattice). Further, the second straight section 160 may serve as an acceleration section. The acceleration section includes an RF acceleration system which may accelerate the injected ion bunches for medical treatment at a maximum kinetic energy of 206 MeV for protons and 400 MeV/u for carbon $C^{5+}$ ions.

Figure 2:
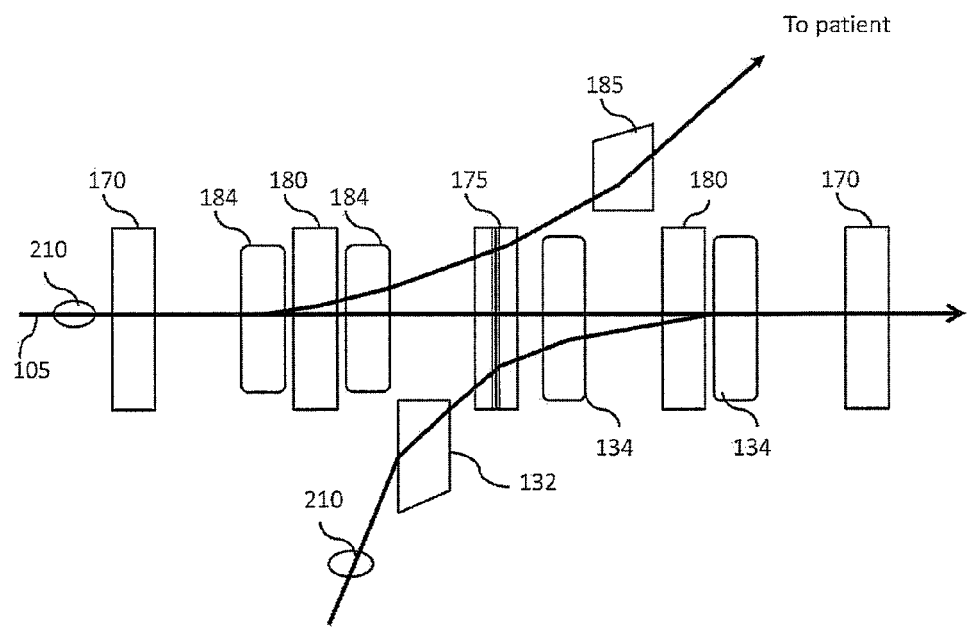
FIG. 2 is a diagram illustrating a system for injecting and extracting ion particles, according to an embodiment of the invention.

FIG. 2 is a block diagram of an embodiment of the straight section 140 serving as an injection/extraction section. A septum magnet 132 may receive a beam bunch 210 from the injection line 130 of FIG. 1. The septum magnet 132 directs the beam bunch 210 towards a pair of injection kickers 134 which in turn direct the beam bunch 210 into the central orbit 105. The injection/extraction section may further include several multipole magnets, such as for example defocusing quadrupole magnets 170, focusing quadrupole magnets 180, and a central defocusing quadrupole magnet 175. The quadrupole magnets may be arranged such as to alternate focusing and defocusing quadrupole magnets. The central defocusing quadrupole magnet 175 may be the same as the other quadrupole magnets, or may have a larger aperture than the other quadrupole magnets in order to allow for the displaced beam to pass though without hitting the beam pipe. Straight section 140 may include fewer or more multipole magnets than depicted in FIG. 2, for example straight section 140 may include between 3 and 9, or between 5 and 7, multipole (e.g., quadrupole) magnets. The injection/extraction section may further include a pair of extraction kickers 184 which extract the beam bunch 210 from the central orbit 105 and into an extraction septum 185 and further to a treatment path for delivering the beam bunch 210 to the malignant tissue.

Embodiments of the invention also encompass a "turn-by-turn" extraction method in which ion particles of the beam bunch 210 are peeled from the beam bunch 210 during each turn of the beam bunch 210 in the synchrotron 100. In theory, any number of ion particles may be peeled during each turn, ranging from a few ion particles to the entire beam bunch. For example, the number of particles being extracted during each turn may be from a lower limit of about $1.0\times10^3$, $1.5\times10^3$, $2.0\times10^3$, $2.5\times10^3$, $3.0\times10^3$, $3.5\times10^3$, $4.0\times10^3$, $4.5\times10^3$, $5.0\times10^3$, $5.5\times10^3$, $6.0\times10^3$, $6.5\times10^3$, $7.0\times10^3$, $7.5\times10^3$, $8.0\times10^3$, $8.5\times10^3$, $9.0\times10^3$, $9.5\times10^3$, $1.0\times10^4$, $1.5\times10^4$, $2.0\times10^4$, $2.5\times10^4$, $3.0\times10^4$, $3.5\times10^4$, $4.0\times10^4$, $4.5\times10^4$, $5.0\times10^4$, $5.5\times10^4$, $6.0\times10^4$, $6.5\times10^4$, $7.0\times10^4$, $7.5\times10^4$, $8.0\times10^4$, $9.0\times10^4$, $10^5$, $10^6$, or $10^7$ to an upper limit of about $2.0\times10^3$, $2.5\times10^3$, $3.0\times10^3$, $3.5\times10^3$, $4.0\times10^3$, $4.5\times10^3$, $5.0\times10^3$, $5.5\times10^3$, $6.0\times10^3$, $6.5\times10^3$, $7.0\times10^3$, $7.5\times10^3$, $8.0\times10^3$, $8.5\times10^3$, $9.0\times10^3$, $9.5\times10^3$, $1.0\times10^4$, $1.5\times10^4$, $2.0\times10^4$, $2.5\times10^4$, $3.0\times10^4$, $3.5\times10^4$, $4.0\times10^4$, $4.5\times10^4$, $5.0\times10^4$, $5.5\times10^4$, $6.0\times10^4$, $6.5\times10^4$, $7.0\times10^4$, $7.5\times10^4$, $8.0\times10^4$, $9.0\times10^4$, $10^5$, $10^6$, $10^7$, $10^8$, $2\times10^8$, $3\times10^8$, $4\times10^8$, $5\times10^8$, $6\times10^8$, $7\times10^8$, $8\times10^8$, $9\times10^8$, $10^9$, $2\times10^9$, $3\times10^9$, $4\times10^9$, $5\times10^9$, $6\times10^9$, $7\times10^9$, $8\times10^9$, $9\times10^9$ or $10^{10}$.

In an embodiment of the invention, between about $1.0\times10^4$ and about $9.0\times10^4$ charged carbon particles are peeled during each turn of the beam bunch 210 in the synchrotron 100. All individual values and subranges between about $1.0\times10^4$ and about $8.5\times10^4$ are included herein and disclosed herein; for example, the number of particles being extracted during each turn may be from a lower limit of about $1.0\times10^4$, $1.5\times10^4$, $2.0\times10^4$, $2.5\times10^4$, $3.0\times10^4$, $3.5\times10^4$, $4.0\times10^4$, $4.5\times10^4$, $5.0\times10^4$, $5.5\times10^4$, $6.0\times10^4$, $6.5\times10^4$, $7.0\times10^4$, $7.5\times10^4$, or $8.0\times10^4$, to an upper limit of about $2.5\times10^4$, $3.0\times10^4$, $3.5\times10^4$, $4.0\times10^4$, $4.5\times10^4$, $5.0\times10^4$, $5.5\times10^4$, $6.0\times10^4$, $6.5\times10^4$, $7.0\times10^4$, $7.5\times10^4$, $8.0\times10^4$, $8.5\times10^4$, or $9.0\times10^4$. In one embodiment, about $4.5\times10^4$ charged carbon particles are peeled during each turn in the synchrotron from the about $10^8$ carbon ions per bunch of the injected beam bunch 210.

Figure 3:
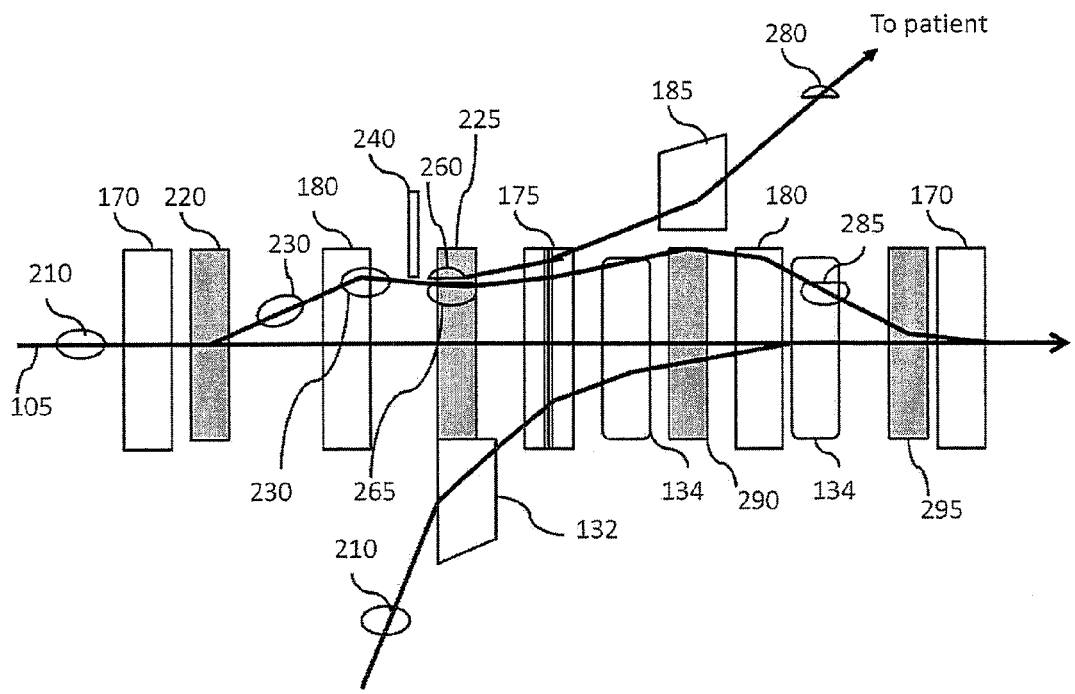
FIG. 3 is a diagram illustrating a system for injecting and extracting ion particles, according to an embodiment of the invention.

FIG. 3 is a block diagram of the components that may be used in such a "turn-by-turn" extraction method, according to embodiments of the invention. The straight section 140 of the synchrotron 100 may be equipped with a low field dipole magnet 220 which can generate an "orbit bump" to deflect the beam orbit in about 5-10 msec. A deflected beam bunch 230 may be deflected between about 1 mm and about 20 mm from the central orbit 105. All individual values and subranges between about 1 mm and about 20 mm group are included herein and disclosed herein; for example, the deflected beam bunch 230 may be deflected from a lower limit of about 1, 2, 3, 4, 5, 6, 7, 8, 9, 10, 12, 14 or 15 mm to an upper limit of about 5, 6, 7, 8, 9, 10, 12, 14, 15, 17, 18, or 20 mm.

A stripping foil 240 may be located at a specified location along the orbit bump. The stripping foil 240 may be able to fully strip at least one electron from the ions of the beam bunch which are deflected enough to pass through the stripping foil 240. The stripping foil 240 may be positioned so that a portion of the deflected beam bunch 230 (e.g., about $4.5\times10^4$ carbon ions) pass through the stripping foil 240 per beam bunch orbit. The stripping foil 240 may be made of gold, tungsten or a lightweight material, such as beryllium, a lithium hydride, or a carbon sheet. In one embodiment, the stripping foil 240 is a carbon sheet. The foil may be between 0.5 micron and 30 microns thick. All individual values and subranges between about 0.5 micron and about 20 microns are included herein and disclosed herein; for example, the foil may have a thickness from a lower limit of about 0.5, 1, 2, 3, 4, 5, 6, 7, 8, 9, 10, 12, 14, 15, 17, 18, 20, or 22 micron to an upper limit of about 5, 6, 7, 8, 9, 10, 12, 14, 15, 17, 18, 20, 22, 25, 26, 27, 28, or 30 micron. The thickness and the material of the foil is selected in order to fully strip the passing particles of electrons, yet at the same time not noticeably reduce the energy of the particles.

The optimum location of the stripping foil may 240 be chosen by taking into consideration two factors. One factor is the first order transfer matrix (R-matrix) between the stripping foil 240 and the entrance of the septum magnet 185, and another other factor is the beam size at the location of the stripping foil 240. The first order transfer matrix between the stripping foil 240 and the entrance of the septum magnet 185 determines the relative displacement of the stripped beam with respect to the circulating beam. The beam size at the location of the stripping foil will permit to strip from the beam a well determined amount of ions (as mentioned, for example, about $4.5 \times 10^4$ carbon ions). The lateral and angular displacements ($\Delta x$, $\Delta x'$) of the central orbit of a fully stripped beam $C^{+6}$ relative to that of a non-stripped beam $C^{+5}$, at the entrance of the septum 310 is given by the following formulas (3) and (4) below.

$$\Delta x_{atSeptum} = (R_{11}(C^{6+}) - R_{11}(C^{5+}))x_{foil} + (R_{12}(C^{6+}) - R_{12}(C^{5+}))x_{foil}' + (R_{16}(C^{6+}) - R_{16}(C^{5+}))\delta \quad (3)$$

$$\Delta x_{atSeptum}' = (R_{21}(C^{6+}) - R_{21}(C^{5+}))x_{foil} + (R_{22}(C^{6+}) - R_{23}(C^{5+}))x_{foil}' + (R_{26}(C^{6+}) - R_{26}(C^{5+}))\delta \quad (4)$$

In the expressions (3) and (4) above the symbols $R_{ij}$, are the first order transfer matrix elements between the location of the foil 240 and the entrance of the septum 310, the symbol $\delta$ is the relative momentum spread of the particles, and the symbols $x_{foil}$, and $x'_{foil}$ are the particle displacement and divergence respectively of the central orbit at the location of the foil. The matrix elements $R_{ij}(C^{6+})$, and $R_{ij}(C^{5+})$ are different for the two types of ions due to the rigidity of the ions.

The ion bunch after the stripping foil 240 includes a stripped ion bunch 260 which may contain $C^{+6}$ ions and an ion bunch 265 which has not been stripped of electrons (which may still contain $C^{+5}$ ions). A second low field dipole magnet 225 may then further bump both the stripped ion bunch 260 and the ion bunch 265. Furthermore, both the stripped ion bunch 260 and the ion bunch 265 may pass through the defocusing central quadrupole magnet 175. Due to lower rigidity, the $C^{+6}$ ions are deflected more than the $C^{+5}$ ions when both pass through the low field dipole magnet 225 and defocusing central quadrupole 175. Subsequently, the $C^{+6}$ ions of stripped ion bunch 260 enter the extraction septum 185 to be further deflected (stripped ion bunch 280) and extracted to a treatment path for delivering the stripped ion bunch 280 to the malignant tissue for treating a patient. The non-stripped ion bunch 285 passes through a pair of low field dipole magnets 290 and 295 which direct the non-stripped ion bunch 285 back into the central orbit 105.

Figure 4:
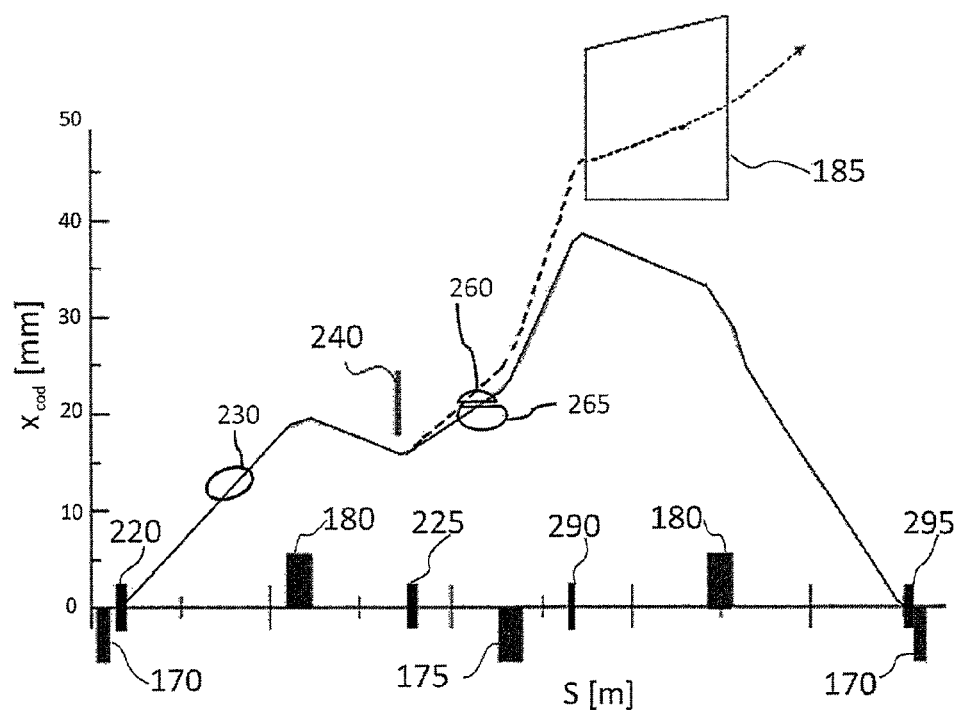
FIG. 4 is a graph showing ion beam deflection, according to an embodiment of the invention.

The result of calculations which model the "orbit bump" displacement is shown in FIG. 4. The "orbit bump" displacement is indicated in millimeters on the y axis of the graph. The graph also indicates on the x axis of the graph the location (in meters) of the four dipole magnets 220, 225, 290, and 295 which create the local displacement of the ion bunch 230 (e.g., $C^{+5}$) along the straight section. The graph further shows the location of the quadrupole magnets 170, 175, and 180, and how the focusing quadrupole magnets 180 may deflect the beam back toward the central orbit 105 and how the defocusing quadrupole magnet 175 may deflect the beam further from the central orbit 105. The dashed trace is the orbit deflection of the stripped ion bunch 260 (e.g., $C^{+6}$ ions) which have been stripped by the stripping foil of at least one electron (e.g., $C^{+5} \rightarrow C^{+6}$). Due to the lower rigidity the stripped ion bunch 260 is deflected more than the ion bunch 265 when both enter the low field dipole magnet 225 located just after the foil 240. Furthermore, the defocusing quadrupole located 175 at the center of the straight section may also further deflect the stripped ion bunch 260 than the ion bunch 265. The stripped ion bunch 260 having been deflected more than the ion bunch 265, enters the high field region of the septum magnet 185 to be extracted towards the delivery system to the patient, while the ion bunch 265 continue on the closed orbit (solid line) via the low field dipole magnets 290 and 295 and the focusing quadrupole magnet 180 to be further accelerated and pass again in the next turn by the stripping foil which will strip part of the ion bunch again.

In certain embodiments, single beam bunches may be injected, accelerated, and extracted at a frequency of 15 Hz. This high frequency of operation is accomplished by making the main magnets of the synchrotron ring part of an LRC resonant circuit which may resonate at 15 Hz, and may be powered by a single resonant power supply.

Figure 5:
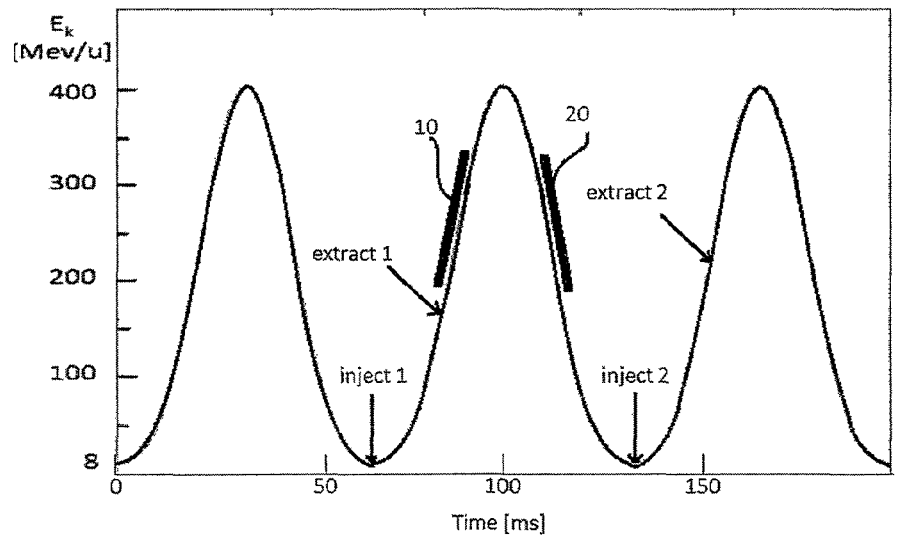
FIG. 5 is a graph showing particle bunch energy as a function of time, according to an embodiment of the invention.

FIG. 5 is a plot of the energy of the circulating beam bunch versus time. The beam bunch may be injected into the synchrotron 10 at the minima (inject 1, inject 2) of the curve shown in FIG. 5 and it may be extracted at any time during the acceleration cycle, as it is indicated by the arrows (extract 1, extract 2). An extraction bar 10 shown in FIG. 5 corresponds to an example of a possible energy range of the extracted beam during the "turn-by-turn" extraction method described above. This energy range for the turn-by-turn beam extraction method can be easily controlled as known by one of ordinary skill in the art. Alternatively, the extraction range may take place as the energy of the beam bunch is decreasing (extraction bar 20), or both increasing (extraction bar 10) and decreasing (extraction bar 20).

The energy levels of the circulating beam bunch at the point of extraction may be between about 50 MeV/u and about 400 MeV/u. All individual values and subranges between about 50 MeV/u and about 400 MeV/u are included herein and disclosed herein; for example, the energy level may be from a lower limit of about 50, 75, 80, 85, 100, 125, 150, 175, 200, 250, 275, 300, 325, or 350 MeV/u to an upper limit of about 80, 85, 100, 125, 150, 175, 200, 250, 275, 300, 325, 350, 375, or 400 MeV/u.

Figure 6:
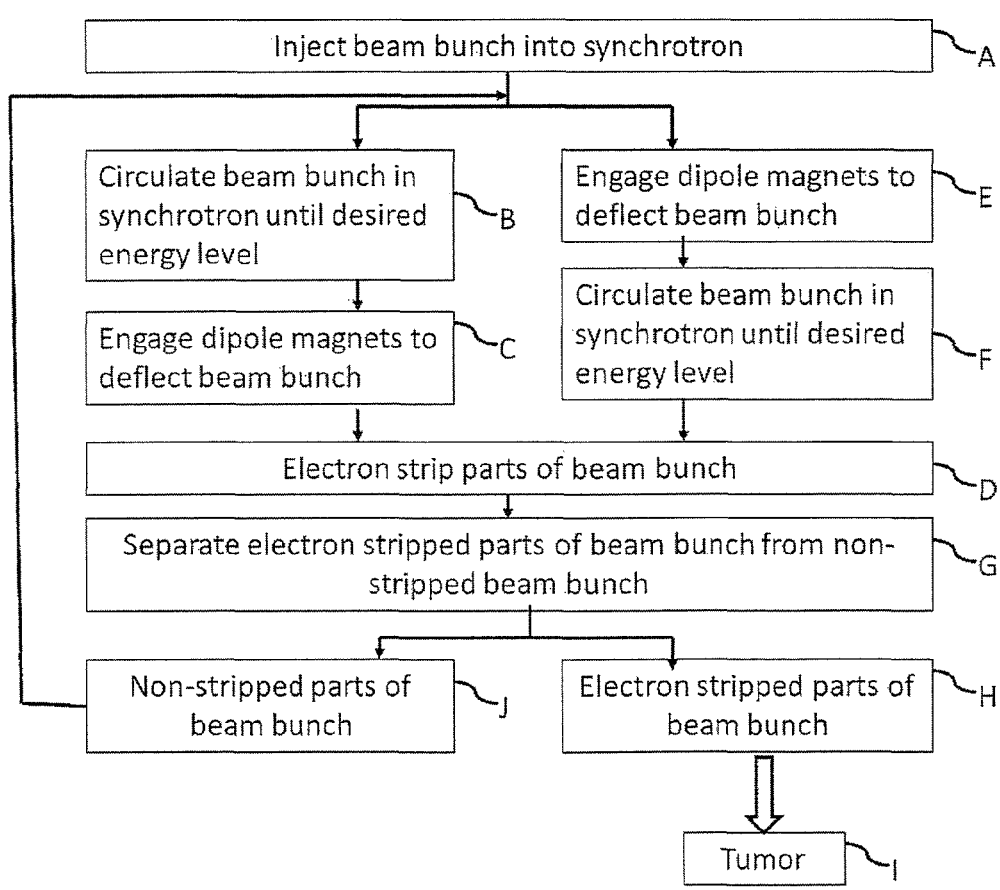
FIG. 6 is a flow chart describing an extraction process, according to an embodiment of the invention.

FIG. 6 is a flow chart summarizing the extraction process described above. First, the beam bunch is injected (#A) into the synchrotron accelerator 100. At least two pathways are then possible: 1) The beam bunch may circulate in the synchrotron central orbit 105 until a desired energy level is obtained (#B), upon which the dipole magnets are engaged (#C) to deflect the beam bunch from the central orbit 105; the orbit bump pushes the circulating beam into the stripping foil (#D) such that some of the $C^{+5}$ ions of the beam pass through the foil to be stripped down to $C^{+6}$ ions. 2) The second pathway is to engage the dipole magnets and deflect the beam bunch (#E) before the desired energy level is reached; when the circulating carbon ions reach the desired energy (#F), the orbit bump pushes the circulating beam into the stripping foil (#D) such that some of the $C^{+5}$ ions of the beam pass through the foil to be stripped down to $C^{+6}$ ions. 3) For both pathways, the stripped ions and non-stripped ions are separated (#G) with the electron stripped parts of the beam bunch (#H) being directed towards the malignant tumor (#I). The non-stripped ion beam bunch (#J) is then cycled through the process again, until another beam bunch is introduced into the synchrotron and the entire cycle is repeated. Thus, it can be seen that it is possible to introduce a beam bunch having $10^8$ particles per bunch and extracting and delivering about $4.5 \times 10^4$ particles per beam bunch cycle in the synchrotron 100, resulting in faster treatment sessions of about 2 minutes for a 1 L tumor.

In another embodiment, simultaneously to the beam bunch being injected into the synchrotron accelerator to be circulated, the dipole magnets are engaged to deflect the beam bunch to circulate close to the foil, but not touching the foil. Then, as the desired energy level is obtained, the dipole magnets are further engaged to further deflect the beam bunch. The subsequent orbit bump pushes the circulating beam into the stripping foil such that some of the $C^{+5}$ ions of the beam pass through the foil to be stripped down to $C^{+6}$ ions. Then, the stripped ions and non-stripped ions are separated with the electron stripped parts of the beam bunch being directed towards the malignant tumor. The non-stripped ion beam bunch is then cycled through the process again, until another beam bunch is introduced into the synchrotron and the entire cycle is repeated.

Although the present invention has been described in considerable detail with reference to certain preferred versions thereof, other versions are possible. Therefore, the spirit and scope of the appended claims should not be limited to the description of the preferred versions contained herein.

The reader's attention is directed to all papers and documents which are filed concurrently with this specification and which are open to public inspection with this specification, and the contents of all such papers and documents are incorporated here by reference.

All the features disclosed in this specification (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalents or similar features.

The invention claimed is:

1. An apparatus for extracting a charged particle beam from a central orbit in a synchrotron, the apparatus comprising:
    at least one first magnet positioned to deflect the charged particle beam from the central orbit to a deflected path;
    at least one stripping foil placed in at least parts of the deflected path, wherein at least a portion of the charged particle beam passing through the stripping foil becomes a stripped charged particle beam;
    at least one second magnet encompassing the central orbit, the stripped charged particle beam, and a remaining charged particle beam, whereby paths of the stripped charged particle beam and the remaining charged particle beam are separated, the path of the stripped charged particle beam being separated further away from the central orbit than is the path of the remaining charged particle beam; and
    at least one particle retainer positioned to return the remaining charged particle beam to the central orbit.

2. The apparatus of claim 1, comprising a septum to further separate the path of the stripped charged particle beam away from the central orbit.

3. The apparatus of claim 1, wherein the at least one first magnet positioned to deflect the charged particle beam comprises at least one dipole magnet.

4. The apparatus of claim 1, wherein the at least one second magnet comprises at least one dipole magnet.

5. The apparatus of claim 4, wherein the at least one second magnet further comprises a multipole magnet.

6. The apparatus of claim 1, wherein the at least one particle retainer comprises at least two dipole magnets.

7. An apparatus for delivering a charged particle beam to treat malignant tissue, comprising:
    a synchrotron having a central orbit;
    at least one first magnet positioned to deflect the charged particle beam from the central orbit to a deflected path;
    at least one stripping foil placed in at least parts of the deflected path, wherein the charged particle beam passing through the stripping foil becomes a stripped charged particle beam;
    a second magnet encompassing the central orbit, the stripped charged particle beam, and a remaining charged particle beam, whereby paths of the stripped charged particle beam and the remaining charged particle beam are separated, the path of the stripped charged particle beam being separated further away from the central orbit than is the path of the remaining charged particle beam;
    at least one particle retainer positioned to return the remaining charged particle beam to the central orbit; and
    a treatment path for delivering the stripped charged particle beam to the malignant tissue.

8. The apparatus of claim 7, comprising a septum to further separate the path of the stripped charged particle beam away from the central orbit.

9. The apparatus of claim 7, wherein the at least one first magnet positioned to deflect the charged particle beam comprises at least one dipole magnet.

10. The apparatus of claim 7, wherein the at least one second magnet comprises at least one dipole magnet.

11. The apparatus of claim 10, wherein the at least one second magnet further comprises a multipole magnet.

12. The apparatus of claim 7, wherein the at least one particle retainer comprises at least two dipole magnets.

13. A method for extracting a charged particle beam from a central orbit in a synchrotron, the method comprising:
    introducing the charged particle beam from an ion source and into the central orbit;
    activating at least one extractor positioned to deflect the charged particle beam from the central orbit;
    passing at least parts of the charged particle beam through at least one stripping foil to provide a stripped charged particle beam;
    passing the stripped charged particle beam and a remaining charged particle beam through at least one magnet encompassing the central orbit, the stripped charged particle beam, and the remaining charged particle beam, such that the paths of the stripped charged particle beam and the remaining deflected charged particle beam are separated, and the path of the stripped charged particle beam is separated further away from the central orbit than is the path of the remaining charged particle beam; and
    activating at least one particle retainer such that the remaining charged particle beam is returned to the central orbit.

14. The method of claim 13, further comprising activating a septum to further separate the path of the stripped charged particle beam away from the central orbit.

15. The method of claim 13, wherein the at least one extractor comprises at least one dipole magnet.

16. The method of claim 13, wherein the at least one particle retainer comprises at least two dipole magnets.

17. The method of claim 13, wherein the at least one magnet encompassing the central orbit, the stripped charged particle beam, and the remaining charged particle beam comprises at least one dipole magnet.

18. The method of claim 17, wherein the at least one magnet encompassing the central orbit, the stripped charged particle beam, and the remaining charged particle beam further comprises at least one multipole magnet.

19. The method of claim 13, wherein the charged particle beam first comprises between about $10^6$ and about $10^{10}$ ion particles per particle bunch.

20. The method of claim 19, wherein the charged particle beam first comprises between about $10^7$ and about $10^9$ ion particles per particle bunch.

21. The method of claim 13, wherein the stripped charged particle beam comprises between about $1.0 \times 10^4$ and about $8.5 \times 10^4$ ion particles per stripped particle bunch.

22. The method of claim 13, wherein the charged particle beam comprises $C^{+5}$ particles.

23. The method of claim 13, wherein the stripped charged particle beam comprises $C^{+6}$ particles.

24. The method of claim 13, wherein the introducing the charged particle beam from an ion source and into the central orbit is performed at a frequency between about 1 Hz and about 75 Hz.

25. The method of claim 24, wherein frequency is between about 10 Hz and 20 Hz.

26. A method for delivering a charged particle beam to treat malignant tissue, comprising:
- introducing the charged particle beam from an ion source and into a central orbit of a synchrotron;
- activating at least one extractor positioned to deflect the charged particle beam from the central orbit to form a deflected charged particle beam;
- allowing at least parts of the deflected charged particle beam to pass through at least one stripping foil such that the deflected charged particle beam passing through the stripping foil becomes a stripped charged particle beam;
- passing the stripped charged particle beam and a remaining deflected charged particle beam through a multi-pole magnet encompassing the central orbit, the stripped charged particle beam, and the remaining deflected charged particle beam, such that the paths of the stripped charged particle beam and the remaining deflected charged particle beam are separated, and the path of the stripped charged particle beam is separated further away from the central orbit than is the path of the remaining deflected charged particle beam;
- activating at least one particle retainer such that the remaining deflected charged particle beam is returned to the central orbit; and
- delivering the stripped charged particle beam to treat malignant tissue.

27. An apparatus for extracting a charged particle beam from a central orbit in a synchrotron, the apparatus comprising:
- at least one extractor positioned to deflect the charged particle beam from the central orbit to a deflected path;
- at least one stripping foil placed in at least parts of the deflected path, wherein the charged particle beam passing through the stripping foil becomes a stripped charged particle beam;
- a multi-pole magnet encompassing the central orbit, the stripped charged particle beam, and a remaining charged particle beam, whereby paths of the stripped charged particle beam and the remaining charged particle beam are separated, and the path of the stripped charged particle and the path of the remaining charged particle beam are separated from the central orbit; and
- at least one particle retainer positioned to return the remaining charged particle beam to the central orbit.

28. The apparatus of claim 27, wherein the path of the stripped charged particle beam is separated further away from the central orbit than is the path of the remaining charged particle beam.

29. The apparatus of claim 28, comprising a septum to further separate the path of the stripped charged particle beam from the central orbit.

* * * * *